(12) United States Patent
Carpino et al.

(10) Patent No.: US 6,407,120 B1
(45) Date of Patent: *Jun. 18, 2002

(54) NEUROPEPTIDE Y ANTAGONISTS

(75) Inventors: Philip A. Carpino, Groton; Marlys Hammond, Salem; Richard F. Hank, North Stonington, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,197

(22) Filed: Jan. 28, 2000

Related U.S. Application Data

(60) Provisional application No. 60/120,593, filed on Feb. 18, 1999.

(51) Int. Cl.[7] ............. A61K 31/4545; A61K 31/444; A61K 31/44; C07D 401/14; C07D 213/56; A61P 25/00

(52) U.S. Cl. ............... 514/318; 514/210.01; 514/237.8; 514/238.2; 514/255.02; 514/331; 514/332; 514/357; 514/424; 514/428; 514/603; 514/616; 514/617; 544/160; 544/165; 544/383; 546/193; 546/194; 546/234; 546/265; 546/337; 548/567; 548/542; 548/950; 564/86; 564/155; 564/181; 564/182

(58) Field of Search ................. 546/193, 194, 546/234, 265, 337; 548/567, 542, 950; 544/160, 165, 383; 564/86, 155, 181, 182; 514/318, 357, 332, 331, 428, 424, 210.01, 237.8, 238.2, 255.02, 603, 616, 617

(56) References Cited

U.S. PATENT DOCUMENTS 5,602,024 A    2/1997    Gerald et al.    ............... 435/325

FOREIGN PATENT DOCUMENTS

| EP | 0184822 | 6/1986 | ......... C07D/213/56 |
| EP | 1027891 | * 1/1999 | |
| EP | 1033366 | 12/2000 | ......... C07D/213/56 |
| JP | 55162757 | 12/1980 | ......... C07D/295/18 |
| WO | 9719682 | 6/1997 | |
| WO | 9720820 | 6/1997 | |
| WO | 9720821 | 6/1997 | |
| WO | 9720822 | 6/1997 | |
| WO | 9720823 | 6/1997 | |
| WO | WO9835957 | 8/1998 | |

OTHER PUBLICATIONS

Dialog®File 351:Derwent WPI, Ihara Chem Ind Co Ltd, Patent Abstracts of Japan, JP 55 162757A, 1980.
Hassner, A., et al., *J. Chem. Soc., Perkin Trans.*, 1(4): 733–7, 1988.
Horhold, H. and Eibish, H., *Tetrahedron*, 25: 4277–4286, 1969.
Ionescu, M. et al., Stud, Univ. Babes–Bolyai. Ser. Chem., 13(1): 95–97, 1969.
Muramatsu, M., et al., *Tetrahedron Letters*, 23: 2133–2136, 1973.
Stevens, C. and French, J., *J. Am. Chem. Soc.*, 75: 657–660, 1953.
Topliss, J. G., et al., *Journal of Organic Chemistry*, 28: 2595–2598, 1963.

* cited by examiner

*Primary Examiner*—Evelyn Mei Huang
(74) *Attorney, Agent, or Firm*—Peter C. Richardson; Gregg C. Benson; Gabriel L. Kleiman

(57) ABSTRACT

The compound

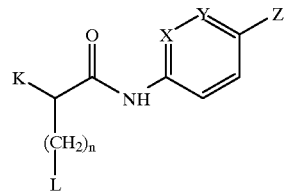

is a neuropeptide Y antagonist and is effective in treating feeding disorders, cardiovascular diseases and other physiological disorders.

19 Claims, No Drawings

NEUROPEPTIDE Y ANTAGONISTS

This application is filed claiming priority from U.S. Provisional Application No. 60/120,593 filed Feb. 18, 1999.

BACKGROUND OF INVENTION

1. Field of the Invention

This invention relates to the use of substituted amides which selectively bind to mammalian Neuropeptide receptors. It further relates to the use of these compounds and compositions containing these compounds in treating conditions related to an excess of neuropeptide Y such as feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of neuropeptide Y1 receptors is related to vasoconstriction, Wahlestedt et al. *Regul. Peptides*, 13: 307–318 (1986), McCauley and Westfall, *J. Pharmacol. Exp. Ther.* 261:863–868 (1992), and Grundemar et al., *Br. J. Pharmacol.* 105:45–50 (1992); and to stimulation of consummatory behavior, Flood and Morley, *Peptides*, 10:963–966 (1989), Leibowitz and Alexander, *Peptides*, 12:1251–1260 (1991), and Stanley et al. *Peptides*, 13:581–587 (1992).

Grundemar and Hakanson. *TiPS*, May 1994 [Vol.15], 153–159, state that, in animals, neuropeptide Y is a powerful stimulus of food intake, and an inducer of vasoconstriction leading to hypertension. They further point out that low levels of neuropeptide Y (NPY) are associated with loss of appetite. These reports clearly indicate that compounds that inhibit the activity of this protein will reduce hypertension and appetite in animals.

EP0759441 and U.S. Pat. No. 5,576,337 report that physiological disorders related to an excess of neuropeptide Y include:

- disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure; conditions related to increased sympathetic nerve activity for example, during or after coronary artery surgery, and operations and sugery in the gastrointestinal tract;
- cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia;
- conditions related to pain or nociception;
- diseases related to abnormal gastrointenstinal motility and secretion, such as different forms of ileus, urinary incontinence, and Crohn's disease;
- abnormal drink and food intake disorders, such as anorexia and metabolic disorders; diseases related to sexual dysfunction and reproductive disorders;
- conditions or disorders associated with inflammation;
- respiratory diseases, such as asthma and conditions related to asthma and bronchoconstriction; and diseases related to abnormal hormone release, such as leutinizing hormone, growth hormone, insulin, and prolactin.

WO 96/14307 describes substituted benzylamine derivatives which selectively bind to human neuropeptide Y1 receptors.

SUMMARY OF THE INVENTION

This invention provides a compound of the formula I

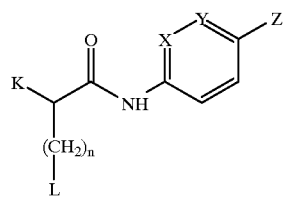

wherein:

K is phenyl, 2-pyridyl, 3-pyridyl or 4-pyridyl, each ring optionally substituted with one to three substituents selected from halogen, $C_1$–$C_3$ alkyl, $C_1$–$C_3$ perfluoroalkyl, $C_1$–$C_3$ alkoxy and $C_1$–$C_3$ perfluoroalkoxy;

L is H, $C_3$–$C_8$ cycloalkyl,

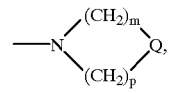

phenyl, 2-pyridyl, 3-pyridyl or 4-pyridyl;

wherein each phenyl and pyridyl ring may be substituted with one to three substituents selected from $C_1$–$C_3$ alkyl, $C_1$–$C_3$ alkoxy and halogen;

Z is —$COR^3$, —$CONR^1R^2$, —$NR^1R^2$ and $SO_2R^4$;

X and Y are CH or N, with the proviso that one of X and Y must be CH;

n is an integer from 0 to 3;

m and p are independently selected from the integers 1 to 3;

Q is O, NR, CHR;

R is hydrogen or $C_1$–$C_6$ alkyl;

$R^1$ and $R^2$ are independently selected from hydrogen, $C_1$–$C_6$ alkyl, $(CH_2)_m$ phenyl, $(CH_2)_m$ pyridyl, or $R^1$ and $R^2$ may be taken together with the nitrogen to which they are attached to form a 4 to 8 numbered ring optionally containing O, NH or NR;

$R^3$ is $C_1$–$C_6$ alkyl; $R^4$ is —$NR_1R_2$,

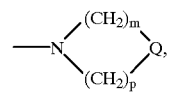

—$NH(CH_2)_m$ phenyl, —$N(C_4$–$C_8$cycloalkyl$)_2$ and —$NH(C_4$–$C_8$ cycloalkyl); or a pharmaceutically acceptable salt thereof;

and with the provisio that when n is zero, K and L are phenyl, and both of X and Y are carbon, then Z may not be —$N(C_2H_5)_2$ or

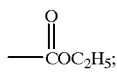

and with the further proviso that if K is phenyl, L may not be hydrogen.

In another aspect, this invention provides a compound of formula I wherein n is zero. This invention also provides a compound of formula I wherein n is zero and L is 2-pyridyl or 4-pyridyl and Z is —N(C$_2$H$_5$)$_2$,

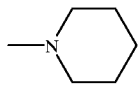

or —SO$_2$N(C$_2$H$_5$)$_2$.

This invention further provides a compound formula I wherein n is zero, Y is N and Z

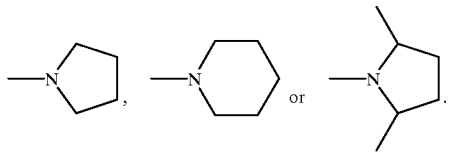

This invention also provides a compound of formula I wherein n is zero, Z is —SO$_2$R$^4$, wherein R$^4$ is —N(C$_2$H$_5$)$_2$ or N(CH$_3$)$_2$.

This invention also provides a compound of formula I selected from the group consisting of:
- N-(4-Diethylamino-phenyl)-2-phenyl-2-pyridin-4-yl-acetamide;
- 2-(4-Fluoro-phenyl)-2-pyridin-4-yl-N-(3,4,5,6-tetrahydro-2H-[1,2']bipyridinyl-5'-yl)-acetamide;
- 2-Phenyl-2-pyridin-4-yl-N-(3,4,5,6-tetrahydro-2H-[1,2']bipyridinyl-5'-yl)-acetamide;
- N-(4-Diethylamino-phenyl)-2-phenyl-2-pyridin-2-yl-acetamide;
- N-(4-Diethyl-sulfamoyl-phenyl)-2-phenyl-2-pyridin-4-yl-acetamide;
- N-(6-Diethylamino-pyridin-3-yl)-2,2-diphenylacetamide;
- 2,2-Diphenyl-N-(6-pyrrolidin-1-yl-pyridin-3-yl)-acetamide;
- 2,2-Diphenyl-N-(3,4,5,6-tetrahydro-2H-[1,2']bipyridinyl-5'-yl)-acetamide;
- N-[6-(2,5-Dimethyl-pyrrolidin-1-yl)-pyridin-3-yl]-2,2-diphenyl-acetamide;
- N-(4-Diethylsulfamoyl-phenyl)-2,2-diphenyl-acetamide; and
- N-(4-Dimethylsulfamoyl-phenyl)-2,2-diphenyl-acetamide.

In another aspect, this invention comprises a method of inhibiting or alleviating a pathological condition or physiological disorder in a mammal characterized by or associated with an excess of neuropeptide Y which accompanies administering to a mammal in need of such treatment a neuropeptide Y inhibiting amount of the compound of Formula I shown above.

This invention also comprises a method of treating a pathological condition wherein said pathological condition or physiological disorder is a feeding disorder such as obesity or bulimia.

In another aspect, this invention comprises a method of inhibiting or alleviating a pathological condition or physiological disorder in a mammal wherein said pathological condition or physiological disorder is selected from the group consisting of:
- disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;
- conditions related to increased sympathetic nerve activity for example, during or after coronary artery surgery, and operations and surgery in the gastrointestinal tract;
- cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;
- conditions related to pain or nociception;
- diseases related to abnormal gastrointenstinal motility and secretion, such as different forms of ileus, urinary incontinence, and Crohn's disease;
- abnormal drink and food intake disorders, such as anorexia and metabolic disorders;
- diseases related to sexual dysfunction and reproductive disorders;
- conditions or disorders associated with inflammation;
- respiratory diseases, such as asthma and conditions related to asthma and bronchoconstriction; and diseases related to abnormal hormone release, such as leutinizing hormone, growth hormone, insulin, and prolactin.

This invention also includes a pharmaceutical composition for inhibiting or alleviating a pathological condition or physiological disorder in a mammal characterized by or associated with an excess of neuropeptide Y, which comprises a compound of formula I or a pharmaceutically acceptable salt thereof and a pharmaceutically acceptable carrier.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

DETAILED DESCRIPTION OF THE INVENTION

The term "pharmaceutically acceptable salt(s)", as used herein, unless otherwise indicated, includes salts of acidic or basic groups that may be present in the compounds of formula I. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As used herein, the term "alkyl" means a straight or branched saturated carbon chain of the specified number of carbon atoms. "Cycloalkyl" means a carbocyclic ring of the designated number of carbon atoms. Each cycloalkyl ring may be optionally substituted with one to three R groups wherein R is $C_1$–$C_6$ alkyl.

"Halogen" means F, Cl, Br or I.

The preparation of compounds of Formula I of the present invention may be carried out in sequential or convergent synthetic routes. Syntheses describing the preparation of the compounds of the invention are shown in the following Schemes. The skills required for carrying out the reaction and purification of the resulting products are known to those in the art. Purification procedures include crystallization and normal phase or reverse phase chromatography.

Scheme 1

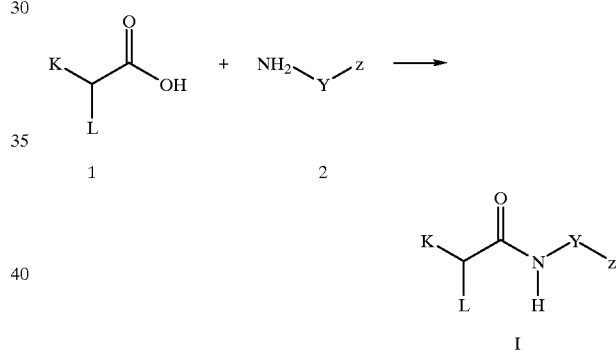

Acids of formula 3(Ra=H) can be coupled to amines of formula 2 using a suitable coupling agent such as EDC, DCC or BOP and an activating catalyst such as HOAT or HOBT in inert solvent such as $CH_2Cl_2$ or DMF to give compounds of the invention such as I. Alternatively, the compounds of formula 3(Ra=H) can be treated with thionyl chloride or oxalyl chloride to generate an intermediate acyl chloride which can be treated with the amine 2 in the presence of an activating catalyst such as DMAP and a base such as triethylamine in an inert solvent such as $CH_2Cl_2$. These conditions are referred to hereafter as standard amino acid coupling conditions.

Scheme 2

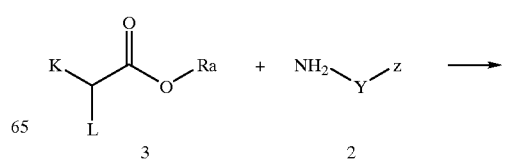

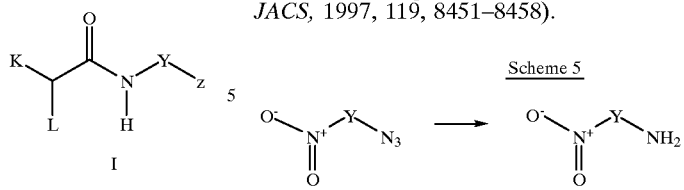

In an alternate route to compounds of formula I, esters of formula 3 (Ra=alkyl) can be coupled to amines of formula 2 using a suitable coupling reagent such as trimethylaluminum in an inert solvent such as toluene. Hydroxysuccimin-imides of formula 3 (Ra=succinimide) can be treated with amines of formula 2 in the presence of a base such as triethylamine in a suitable polar solvent such as dioxane/water to give compounds of formula I.

6359–6362; Wagaw, S.; Rennels, R. A.; Buchwald, S. L. JACS, 1997, 119, 8451–8458).

Scheme 5

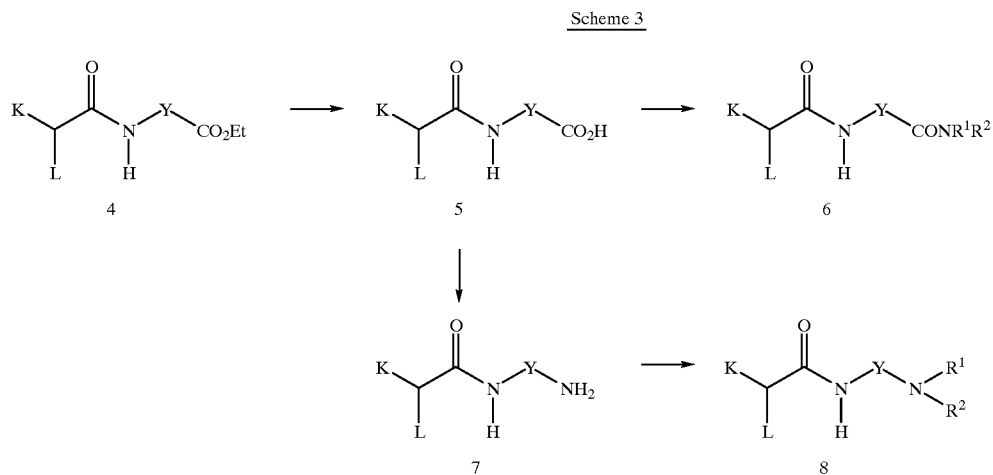

Scheme 3

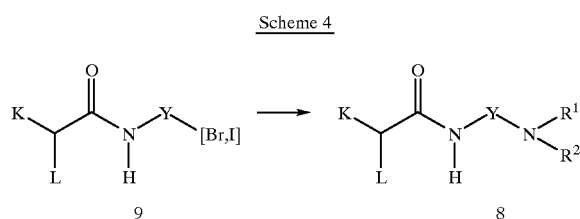

The Z functionality in formula I can be elaborated into the requisite group after amino acid coupling. For example, Z may be introduced as a carboexothy group and then the ester (provided it is the only ester in the molecule) can be saponified into the carboxylic acid such as 5 which can be further derivatized to amides such as 6. The carboxylic acid can also be converted to an amine such as 7 via a Curtius Rearrangement using diphenylphosphoryl azide. Treatment of compounds of formula 7 with aldehydes in a suitable solvent such as HOAc or MeOH, followed by treatment with a reducing agent such as NaBH(OAc)$_3$ will give amines of formula 8.

Scheme 4

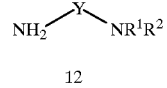

12

Compounds of formula 8 can also be prepared by a palladium-catalyzed amination reaction starting from the appropriate aryl chloride, bromide or iodide such as 9 (see Wolfe, J. P.; Buchwald, S. L. *Tetrahedron Letters,*1997, 38, The amines of formula 2 can be prepared by several procedures depending on the Z functionality. Treatment of a halo-nitro-aromatic compound 10 with an amine in the presence of a base such as sodium hydride in a polar solvent such as DMF at temperatures from 23° C. to 120° C. will provide the aromatic addition product 11. Palladium-catalyzed hydrogenation of 11 in a suitable solvent such as EtOH will provide the amine 12. The reduction of the nitro group can also be carried out using stannic chloride in a suitable solvent such as EtOH. Alternatively, compounds of formula 10 can be treated with NaN$_3$ in a suitable solvent such as DMSO, then reduced using triphenylphosphine in a suitable solvent such as THF/water, converted to the appropriately substituted nitro amines of formula 11, and hydrogenated as described above.

Furthermore, carboxylic acids and nitriles serve as key intermediates in the preparation of amino-substituted heterocycles. Many of the methods are documented in A. R. Katrizky, *Handbook of Heterocyclic Chemistry*, Pergamon Press, 1985, New York, N.Y. and may be used to synthesize a variety of heterocylic compounds of the present invention.

Scheme 6

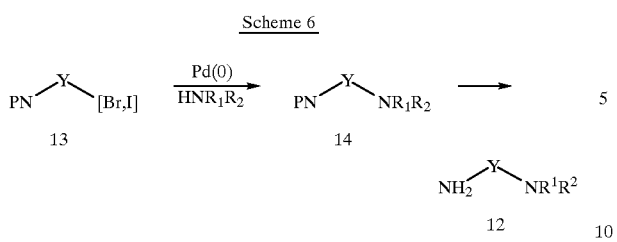

Compounds of formula 12 can also be prepared from a halo-aromatic compound of formula 13 in which the amino group is protected. Treatment of 13 with an appropriate amine using a palladium catalyst such as $Pd_2(DBA)_3$ as described in Buchwald references in the presence of NaO-t-Bu and a phosphine ligand such as $P(o\text{-tolyl})_3$ in a solvent such as toluene at temperatures up to 100° C. will provided the amines of formula 14. Removal of the protecting group using appropriate conditions provides amines of formula 12.

Scheme 7

Amines of formula 17 can be prepared from a nitro-substituted sulfonyl chloride of formula 15. Reaction of 15 with an amine in a suitable inert solvent such as dichloromethane at ambient temperature will provide sulfonamides of formula 16. Reduction of the nitro group of 16 can be carried out using $H_2$ with Pd/C or another suitable reduction catalyst in an appropriate solvent such as ethanol, or using a reducing agent such as tin(II)chloride in an appropriate solvent such as ethanol to provide amines of formula 17.

Scheme 8

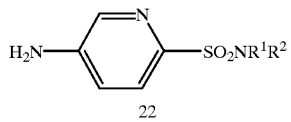

Amines of formula 22 can be prepared beginning with a nitrochloropyridine of formula 18 by treatment with sodium sulfide in an appropriate solvent such as ethanol to provide a nitro disulfide of formula 19. Oxidation of the disulfide under conditions such as chlorine in acetic anhydride or chlorine in an acid such as acetic, sulfuric, or nitric acid at a temperature of –20° C. will provide a nitrosulfonyl chloride of formula 20, which can be treated with an amine ($HNR^1R^2$) in an appropriate solvent such as dichloromethane at ambient temperature to provide a nitrosulfonamide of formula 21. Reduction of the nitro group can be accomplished by hydrogenation over a catalyst such as palladium on carbon, or by treatment with a reducing agent such as tin(II)chloride to provide an aminosulfonamide of formula 22.

Scheme 9

Esters and acids of formulas 1 and 3 can be prepared by a number of procedures, depending upon the nature of the K and L substituents. Treatment of the enolate prepared from esters of formula 23 (Ra=alkyl) with triphenylmethylpyridinium tetrafluoroborate (24) will provide 4-pyridyl esters of formula 25 (see Sammes, M. P.; Lee, C. M.; Katritzky, A. R. *J. Chem. Soc. Perkin Trans.* 1, 1981, 2476–2482.). The ester may be saponified using a suitable base such as sodium hydroxide in an appropriate solvent system such as methanol-water either at ambient temperature or at reflux to provide acids of formula 26.

Scheme 10

-continued

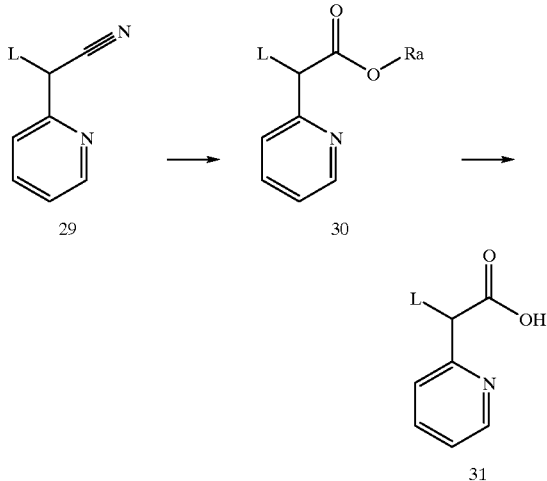

Esters containing a 2-pyridyl substituent can be prepared by addition of the anion of a nitrile of formula 27 prepared with a suitable base such as potassium t-butoxide in an inert solvent such as THF to a 2-bromopyridine of formula 28 in a solvent such as THF at ambient temperature to afford substituted nitrites of formula 29 (see Deutsch, H. M.; Shi, Q.; Gruszecka, E.; Schweri, M. M. *J. Med. Chem.* 1996, 39, 1201–1209). Pinner alcoholysis in refluxing RaOH (Ra= alkyl) saturated with an acid such as HCl will then furnish 2-pyridyl esters of formula 30. The ester may saponified using a suitable base such as sodium hydroxide in an appropriate solvent system such as methanol-water either at ambient temperature or at reflux to provide acids of formula 31.

Scheme 11

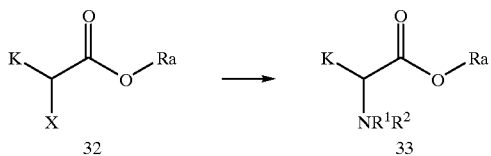

Amino esters of formula 33 can be prepared from a suitable α-halo ester of formula 32 by refluxing with an appropriate amine (HNR$^1$R$^2$) in a suitable solvent such as benzene (see Beuhler, C. A.; Smith, H. A.; Nayak, K. V.; Magee, T. A. *J. Org. Chem.* 1961, 26, 1573–1577; Najer, H.; Charbrier, P.; Guidicelli, R.; Sette, *J. Bull. Soc. Chim. Fr.* 1958, 1189–1192; Henry, R.; Dehn, W. *J. Am. Chem. Soc.* 1950, 72, 2804.)

The pharmaceutical utility of the compound of Formula I is indicated by the following assays for human NPY1 and NPY5 receptor activity.

NPY1 Assay

The procedure used is similar to that described by Gordon et al. (*J. Neurochem.* 55:506–513, 1990). SK-N-MC cells were purchased from ATCC (Rockville, Md.). Cells were maintained at 37° C. and 5% $CO_2$ in Dulbecco's modified essential media (DMEM) with L-glutamine and 110 mg/L sodium pyruvate, which was supplemented with 10% fetal bovine serum and 25 mM HEPES (pH 7.3). The binding assay was performed in 24-well plates (Falcon) when the cells were confluent. Taking care to not disturb the cells on the bottom of the wells, the media was aspirated, and 0.5 ml of Dulbecco's phosphate buffered saline (DPBS) with calcium and magnesium were added to each well. The DPBS was aspirated and an additional aliquot of DPBS was added and aspirated. To begin the assay, binding buffer consisting of serum-free DMEM containing 0.5% bovine serum albumin, 0.1% bacitracin and 0.1 mM phenylmethylsulfonylfluoride was added to each well. The cells and the binding buffer preincubated for 30 minutes at room temperature, at which point the drug dilution and [$^{125}$I]PYY (NEN-DuPont: 50000–75000 cpm~50 pM) were added to yield a final volume of 250 ul. Nonspecific binding was defined with 1 mM NPY (porcine or human, Bachem California). After a 3 hour incubation at room temperature, the plates were then put on ice and the wells were aspirated. The cells were washed 4–6 times with 0.5 ml of ice-cold DPBS. A dilute solution of Triton X-100 (1%) was then added to each well. After approximately 1 hour at room temperature, an aliquot from each well was transferred to a 12×75 mm test tube, and the amount of [$^{125}$I] was quantitated on a gamma counter with an efficiency of 80–85% (Genesys 5000, Laboratory Technologies). $IC_{50}$ values were calculated with the non-linear curve fitting program RS/1 (BBN Software Products Corp., Cambridge, Mass.).

Assay for NPY-5 Binding

[$^{125}$I]PYY Binding at Human NPY Receptors Expressed in Sf9 Cells

Baculovirus-infected Sf9 cells expressing recombinant human NPY 5 receptors are harvested at 48 hours. At the time of harvest, cell pellets are resuspended in lysis buffer (20 mM Tris-HCl, pH 7.4, 5 mM EDTA, 0.5 µg/ml leupeptin, 2 µg/ml Aprotonin and 200 mM PMSF) and homogenized using a Polytron (setting 3, 25–30 seconds). Homogenates are centrifuged at 40° C. for 5 minutes at 200 ×g (~1.5 rpm) to pellet the nuclei. The supernatant is collected into a fresh tube and centrifuged at 48,000 ×g for 10 minutes. Pellets are washed once in lysis buffer and centrifuged. The final pellet is resuspended in PBS and stored in aliquots at –80° C. Purified membranes are washed using PBS and resuspended in binding buffer (50 mM Tris(HCl), pH 7.4, 5 mM KCl, 120 mM NaCl, 2 mM $CaCl_2$, 1 mM $MgCl_2$, 0.1% bovine serum albumin (BSA)). Membranes (20 µg/reaction tube) are added to polypropylene tubes containing 0.035 nM [$^{125}$I]PYY(porcine), displacers ranging from $10^{-12}$ M to $10^{-5}$ M, and buffer to yield a final volume of 0.5 mL. Nonspecific binding is determined in the presence of 1 µM NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mL cold binding buffer without BSA. A gamma counter is used to count filters with an efficiency of 85%. $IC_{50}$ values were calculated with the non-linear curve fitting program RS/1 (SigmaPlot, Jandel).

Functional Assay for NPY Receptors Expressed in Oocytes

Experiments were performed on Xenopus oocytes. Oocytes were prepared and maintained using standard protocols (Dascal and Lotan, in *Methods in Molecular Biology; Protocols in Molecular Neurobiology*, eds. Longstaff & Revest, Humana, Clifton, N.J., 13: 1992). For the present experiments, oocytes were obtained from 6 frogs. Oocytes were recorded from 2–7 days following coinjection of GIRK1 and the H17 NPY-1 or NPY-5 subtype mRNA (25 ng of each, 50 nL total volume).

Two electrode voltage clamp recordings were carried out using a Warner Instruments Oocyte clamp OC 725B. Data were collected on a Macintosh microcomputer and analyzed using Superscope software. Voltage and current electrodes were pulled from glass tubing (1.5 mM O.D.) on a Brown/Flaming micropipet puller (Sutter Instruments, model P-87). Electrodes contained 3M KCl and had resistances of 0.5–2 MOhms. Oocytes were bathed in normal external solution containing; 90 mM NaCl, 1 mM KCl, 1 mM $MgCl_2$, 1 mM $CaCl_2$, 5 mM HEPES, pH=7.4. Before NPY agonists or antagonists were introduced, a high $K^+$ solution containing; 1 mM NaCl, 90 mM KCl, 1 mM $MgCl_2$, 1 mM $CaCl_2$, 5 mM HEPES was applied to permit recording of the inwardly rectifying $K^+$ current. Drugs were applied diluted in the high $K^+$ media.

100 $\mu$M stocks of NPY, PP (pancreatic polypeptide) or NPY peptide fragments or PYY (peptide y) peptide fragments were prepared in water and frozen until needed.

Oocytes were voltage-clamped at −80 mV with two electrodes. Oocytes were initially superfused with normal external medium (approximate flow rate 4 ml/min.). Before drugs were applied, cells were superfused with high $K^+$ solution to permit activation of the inwardly rectifying $K^+$ current. In oocytes coinjected with NPY receptor and GIRK1 mRNA, the NPY agonist induced an additional inward current over the resting $K^+$ current caused by high $K^+$ medium. Because responses desensitized at slow, but varying rates, cumulative dose applications were administered to generate concentration response curves. Two to four doses of agonist were applied to each cell. Agonist dose responses in each cell were normalized against the response to a maximal concentration of human NPY. Dose response curves were fit with a logistic equation using Kaleidagraph software (Abelbeck software, Reading, Pa.).

The compound of formula I and pharmaceutically acceptable salts thereof (the active compound) may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. The active compound may be present in association with one or more non-toxic pharmaceutically acceptable carriers and/or diluents and/or adjuvants and if desired other active ingredients. The pharmaceutical compositions containing the active compound may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil liquid paraffin or olive oil.

Aqueous suspensions contain the active material in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example sweetening, flavoring and coloring agents, may also be present. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The active compound may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The active compound may be administered parenterally in a sterile medium, The drug, depending on the vehicle and concentration used can either be suspended or dissolved in the vehicle. Advantageously, adjuvants such as local anesthetics, preservatives and buffering agents can be dissolved in the vehicle.

Dosage levels of the order of from about 0.1 mg to about 15 mg of active compound per kilogram of body weight per day are useful in the treatment of the above-indicated conditions (about 7 mg to about 1 g per human patient per day). The amount of active compound that may be combined with the carrier materials to produce a single dosage form will vary depending upon the host treated and the particular mode of administration. Dosage unit forms will generally contain between from about 1 mg to about 500 mg of an active compound.

It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

As a consequence of its action in treating pathological conditions the compound of the present invention possess utility for treatment of ungulate animals such as swine, cattle, sheep, and goats. The active compound of the invention can additionally be used for the treatment of household pets, for example companion animals such as dogs and cats. The administration of the active compound of formula I can be effected orally or parenterally. An amount of the active compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active compound can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing the compound of the invention with a sufficient amount of animal feed to provide from about $10^{-3}$ to 500 ppm of the compound in the feed or water.

The preferred medicated swine, cattle, sheep and goat feeds generally contain from 1 to 400 grams of active compound per ton of feed, the optimum amount for these animals usually being about 50 to 300 grams per ton of feed.

The preferred poultry and domestic pet feeds usually contain about 1 to 400 grams and preferably 10 to 400 grams of active compound per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compound of the present invention to provide the animal with 0.01 to 20 mg/kg/day of body weight of the active ingredient. The preferred dosage for poultry, swine, cattle, sheep, goats and domestic pets is in

EXAMPLES

Example 1

N-(4-Diethylamino-phenyl)-2-phenyl-2-pyridin-4-yl-acetamide

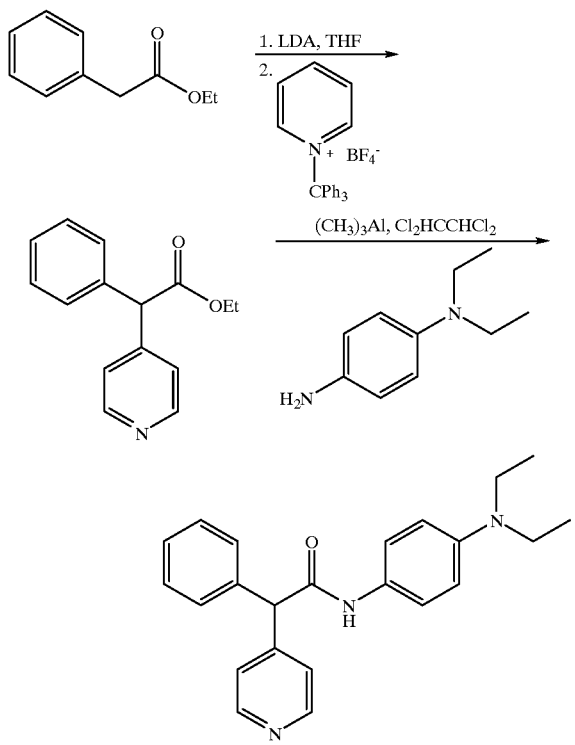

Step A: Ethyl phenylacetate (3.13 g, 19 mmol, 1.0 equiv) was added in a dropwise manner to a solution of LDA (19 mmol, 1 equiv) in THF (30 mL) at −78° C. The resultant solution was maintained at to −78° C. for 25 minutes, and then warmed to 0° C. for 10 minutes. Triphenylmethylpyridinium tetrafluoroborate (7.8 g, 19 mmol, 1.0 equiv) was added in one portion. The reaction mixture was allowed to warm to 23° C. overnight and then concentrated. The residue was partitioned between saturated aqueous ammonium chloride (50 mL) and ethyl acetate (50 mL). The layers were separated, and the aqueous layer was dried over magnesium sulfate and concentrated. The residue was purified by flash column chromatography (25% THF/hexanes) to afford ethyl α-phenylpyridylacetate (2.0 g).

Step B: Trimethylaluminum (2.0 mL of a 2.0 M solution in toluene, 4.0 mmol, 3.0 equiv) was added to a solution of N,N-diethyl-1,4-phenylenediamine (0.68 mL, 4.0 mmol, 3.0 equiv) in 1,2-dichloroethane (10 mL). The resultant solution was stirred at 23° C. for 30 minutes, and then phenyl-pyridin-4-yl-acetic acid ethyl ester (330 mg, 1.36 mmol, 1.0 equiv) was added. The reaction mixture was heated to 60° C. for 19 hours, cooled to 23° C., and quenched with 1 N aqueous tartaric acid. The pH of the reaction mixture was adjusted to 5, and the reaction mixture was extracted with three portions of ethyl acetate (50 mL). The combined organic extracts were dried over magnesium sulfate and were concentrated. Purification of the residue by flash column chromatography (20% THF/hexanes grading to 100% THF) provided N-(4-Diethylamino-phenyl)-2-phenyl-2-pyridin-4-yl-acetamide (160 mg). MS: 360 (M+1)

The compounds in Table 1 were prepared according to the procedure given in Example 1:

TABLE 1

| Ex # | Compound | Structure | Mass Spectrum (MH)+ |
|---|---|---|---|
|  | N-(4-Diethylamino-phenyl)-2-phenyl-2-pyridin-4-yl-acetamide |  | 360 |

TABLE 1-continued

| Ex # | Compound | Structure | Mass Spectrum (MH)+ |
|---|---|---|---|
| | 2-(4-Fluoro-phenyl)-2-pyridin-4-yl-N-(3,4,5,6-tetrahydro-2H-[1,2']bipyridinyl-5'-yl)-acetamide | | 391 |
| | 2-Phenyl-2-pyridin-4-yl-N-(3,4,5,6-tetrahydro-2H-[1,2']bipyridinyl-5'-yl)-acetamide | | 373 |
| | 2-Pyridin-4-yl-N-(3,4,5,6-tetrahydro-2H-[1,2']bipyridinyl-5'-yl)-acetamide | | 297 |
| | N-(4-Diethylamino-phenyl)-2-pyridin-4-yl-butyramide | | 312 |
| | 2-Pyridin-4-yl-N-(3,4,5,6-tetrahydro-2H-[1,2']bipyridinyl-5'-yl)-butyramide | | 325 |

TABLE 1-continued

| Ex # | Compound | Structure | Mass Spectrum (MH)+ |
|---|---|---|---|
| | 2-Pyridin-4-yl-N-(3,4,5,6-tetrahydro-2H-[1,2']bipyridinyl-5'-yl)-propionamide | | 311 |
| | N-(4-Diethylamino-phenyl)-2-pyridin-4-yl-propionamide | | 298 |

Example 2

N-(4-Diethylamino-phenyl)-2-(4-fluoro-phenyl)-2-pyridin-4-yl-acetamide

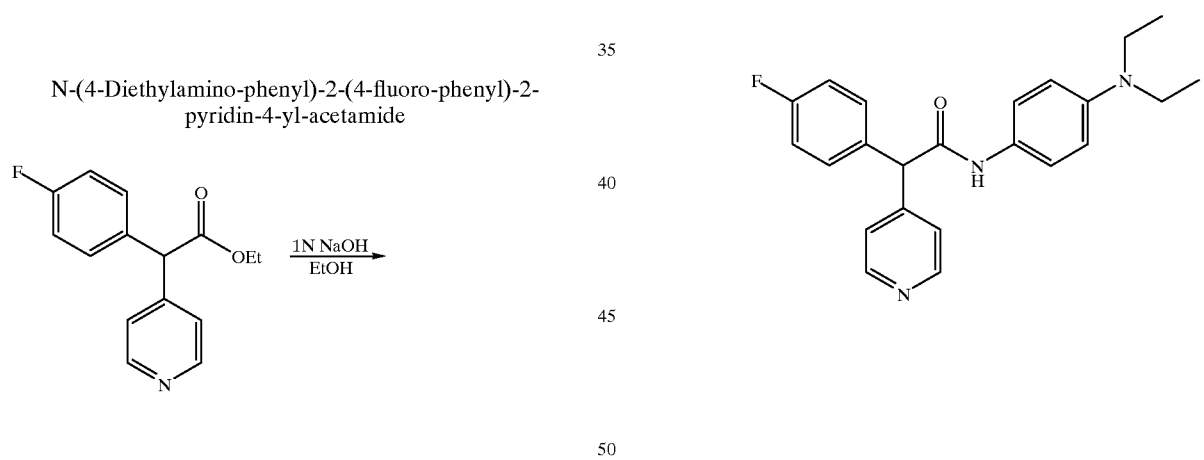

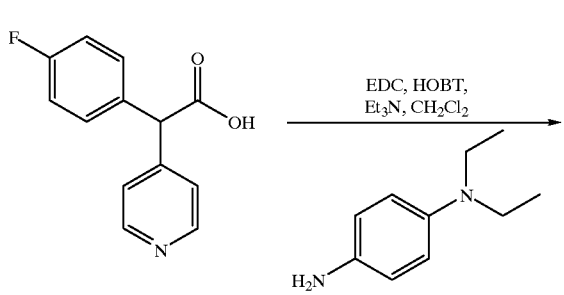

Step A: A solution of sodium hydroxide (0.708 mL of 1N in water, 0.71 mmol, 1.2 equiv) was added to a solution of (4-Fluoro-phenyl)-pyridin-4-yl-acetic acid ethyl ester (153 mg, 0.59 mmol, 1 equiv) in ethanol (25 mL). The resultant solution was maintained at room temperature for 14 hours and then neutralized by the addition of HCl (0.708 mL, 0.708 mmol, 1.2 equiv). Volatiles were removed from the reaction mixture by rotary evaporation and the residue was co-evaporated once with acetone (25 mL) and once with chloroform (25 mL). The crude product was carried directly into the next step.

Step B: 1-(3-dimethylamino)propyl-3-ethylcarbodiimide hydrochloride (EDC, 136 mg, 0.71 mmol, 1.2 equiv) was added to a solution of the crude acid (0.59 mmol, 1.0 equiv), N,N-diethyl-1,4-phenylenediamine (97 mg, 0.59 mmol, 1.0 equiv) and 1-hydroxybenzotriazole (HOBT, 120 mg, 0.89 mmol, 1.5 equiv) in dichloromethane (6 mL) at 23° C. The reaction mixture was stirred at 23° C. for 18 hours, diluted with ethyl acetate (50 mL), washed once with 1N sodium hydroxide (25 mL) and once with 1N hydrochloric acid (25 mL). The organics were dried over magnesium sulfate and concentrated. The residue was purified by flash column chromatography (10% THF/hexanes grading to 20% THF/hexanes) to provide N-(4-Diethylamino-phenyl)-2-(4-fluoro-phenyl)-2-pyridin-4-yl-acetamide (50 mg). MS: 378 (M+1)

The compounds in Table 2 were prepared according to the procedure given in Example 2.

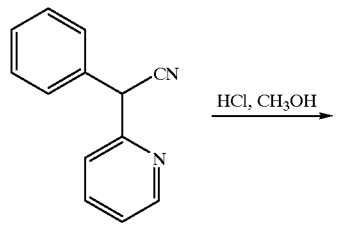

TABLE 2

| Ex # Compound | Structure | Mass Spectrum (MH)+ |
|---|---|---|
| N-(4-Diethylamino-phenyl)-2-(4-fluoro-phenyl)-2-pyridin-4-yl-acetamide | | 378 |
| N-(4-Diethylamino-phenyl)-2-pyridin-3-yl-acetamide | | 284 |
| N-(4-Diethylamino-phenyl)-2-pyridin-4-yl-acetamide | | 284 |

Example 3

N-(4-Diethylamino-phenyl)-2-phenyl-2-piperidin-2-yl-acetamide

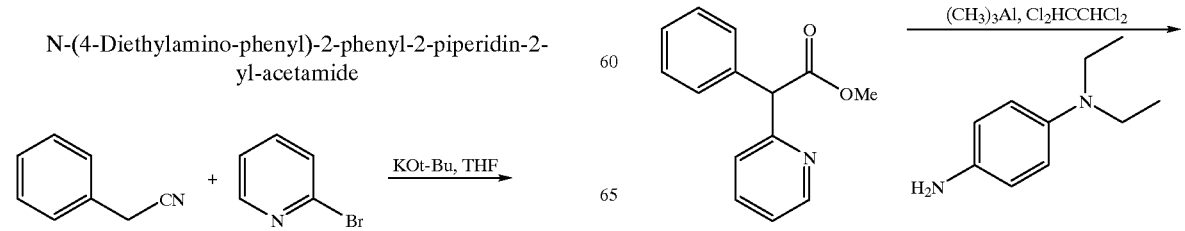

-continued

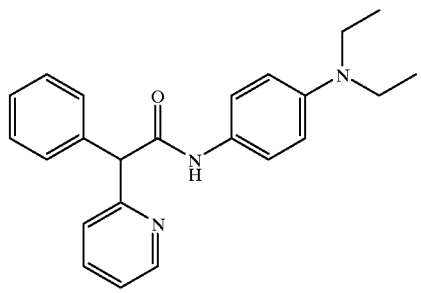

Step A: A solution of phenylacetonitrile (3.0 g, 26 mmol, 1.0 equiv) in THF (5 mL) was added to a solution of potassium tert-butoxide (3.2 g, 28 mmol, 1.1 equiv) in THF (15 mL) at 23° C. The resultant solution was stirred for 30 minutes at 23° C., and then 2-bromopyridine (4.1 g, 26 mmol, 1.0 equiv) in THF (5 mL) was added over an 8-minute period. The resultant suspension was stirred for 1 hour at 23° C., and then heated to reflux for 18 hours. Upon cooling, the reaction mixture was concentrated. The residue taken up in ethyl acetate (100 mL) and washed with three portions of water (50 mL) and three portions of 6 N hydrochloric acid (50 mL). The combined aqueous washings were made basic (pH 12) and were extracted with three portions of ethyl acetate (50 mL). The combined organics were concentrated to provide the crude 2-phenyl-2-(2-pyridine)acetonitrile.

Step B: A suspension of 2-phenyl-2-pyridineacetonitrile (1.8 g, 9.4 mmol, 1.0 equiv) in methanol (20 mL) was cooled to 0° C. and saturated with hydrogen chloride gas for 20 minutes. After warming the reaction mixture to 23° C., it was allowed to stand for 18 hours and then concentrated. The residue was taken up in water (50 mL), the pH of the solution was adjusted to 12 with 1N sodium hydroxide, and the basic solution was extracted with three portions of ethyl acetate (50 mL). The combined organics were dried over magnesium sulfate and were concentrated. Purification of the residue was accomplished by flash column chromatography to afford methyl 2-phenyl-2-(2-pyridyl)acetate (1.1 g).

Step C: According to the procedure given in Example 2, Step B, methyl 2-phenyl-2-(2-pyridyl)acetate (477 mg, 2.1 mmol) was coupled with N,N-diethylphenylenediamine (1.05 mL, 1.04 g, 6.3 mmol) using trimethylaluminum (3.15 mL of a 2.0 M solution in hexane, 6.3 mmol) in 1,2-dichloroethane (20 mL). Standard work-up provided a residue that was purified by flash column chromatography (96:3:1 dichloromethane/methanol/AcOH) to afford the title compound as its diacetate salt. The product was dissolved in methanol and treated with an excess of ethereal HCl to provide the title compound as its bis-HCl salt (687 mg). MS: 360 (M+1)

The compounds in Table 3 were prepared according to the procedure given in Example 3.

TABLE 3

| Ex # | Compound | Structure | Mass Spectrum (MH)+ |
|---|---|---|---|
|  | N-(4-Diethylamino-phenyl)-2-phenyl-2-pyridin-2-yl-acetamide | 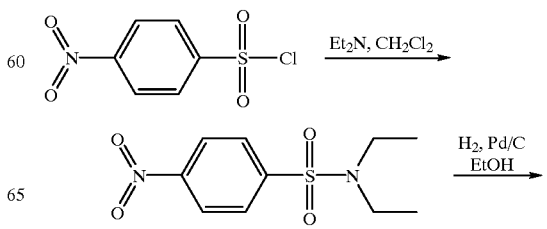 | 360 |

Example 4

N-(4-Diethylsulfamoyl-phenyl)-2-phenyl-2-pyridin-4-yl-acetamide

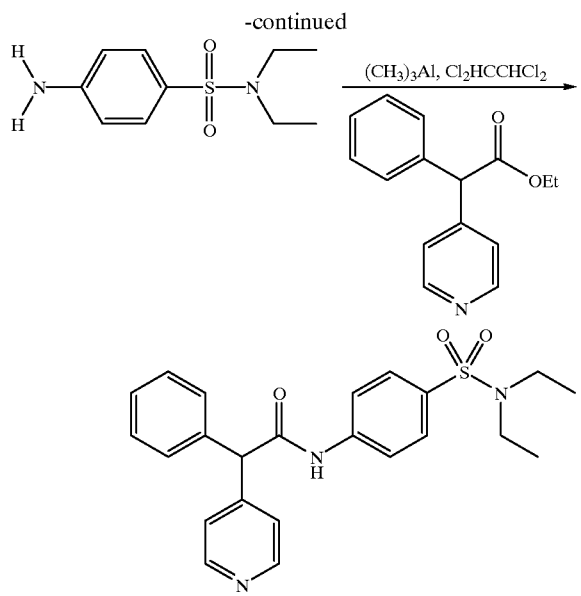

Step A: Diethylamine (0.815 mL, 576 mg, 7.86 mmol) was added in one portion to a solution of 4-nitrobenzenesulfonyl chloride (582 mg, 2.62 mmol) in dichloromethane (10 mL). The resultant solution was stirred at 23° C. for 14 hours and then washed twice with 1N HCl (15 mL). The organics were dried over magnesium sulfate and concentrated to provide N,N-Diethyl-4-nitro-benzenesulfonamide as an off-white solid (617 mg).

Step B: A 250 mL Parr shaker bottle was charged with 4-nitro-N,N-diethyl-benzenesulfonamide (617 mg, 2.39 mmol), ethyl acetate (50 mL), and 10% palladium on activated carbon (100 mg). The bottle was place on a Parr shaker apparatus and charged with hydrogen to a pressure of 52 psi. The reaction mixture was shaken for two hours, filtered through celite, and concentrated to provide 4-Amino-N,N-diethyl-benzenesulfonamide as a green solid (581 mg).

Step C: As described in Example 1, 4-Amino-N,N-diethyl-benzenesulfonamide (242 mg, 1.06 mmol, 2.0 equiv) was coupled with phenyl-pyridin-4-yl-acetic acid ethyl ester (128 mg, 0.53 mmol, 1.0 equiv) using trimethylaluminum (0.53 mL, 0.53 mmol, 2 equiv) in dichloroethane (20 mL). Standard work-up and purification of the residue by rotary chromatography (5% methanol/methylene chloride) provided N-(4-Diethylsulfamoyl-phenyl)-2-phenyl-2-pyridin-4-yl-acetamide (337 mg)

The compounds in Table 4 were prepared according to the procedure given in Example 4.

TABLE 4

| Ex # | Compound | Structure | Mass Spectrum (MH)+ |
|---|---|---|---|
| | N-(4-Diethyl-sulfamoyl-phenyl)-2-phenyl-2-pyridin-4-yl-acetamide | | 424 |
| | N-(4-Diethylsulfamoyl-phenyl)-2-phenyl-2-pyridin-2-yl-acetamide | | 424 |

Example 5

N-(4-Acetyl-phenyl)-2,2-diphenyl-acetamide

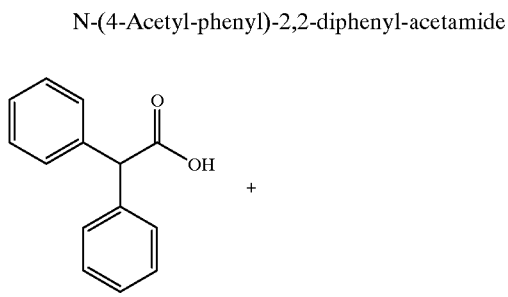

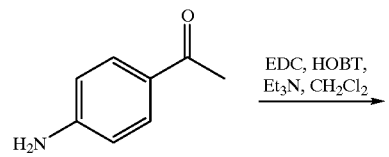

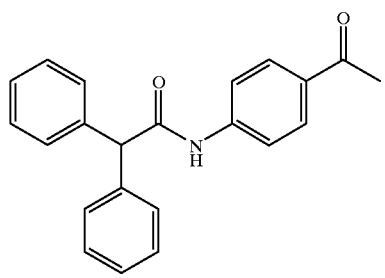

1-(3-Dimethylamino)propyl-3-ethylcarbodiimide hydrochloride (EDC, 210 mg, 1.1 mmol, 1.2 equiv) was added to a solution of acid (190 mg, 0.91 mmol, 1.0 equiv), 4-aminoacetophenone (120 mg, 0.91 mmol, 1.0 equiv) and 1-hydroxybenzotriazole (HOBT, 190 mg, 1.4 mmol, 1.5 equiv) in dichloromethane at 23° C. The reaction mixture was stirred at 23° C. for 18 hours, diluted with ethyl acetate (50 mL), washed once with 1N sodium hydroxide (25 mL) and once with 1N hydrochloric acid (25 mL). The organics were dried over magnesium sulfate and concentrated. The residue was purified by flash column chromatography (25% THF/hexanes) to provide N-(4-Acetyl-phenyl)-2,2-diphenyl-acetamide (140 mg). MS: 330 (M+1)

The compounds in Tables 5a and 5b were prepared according to the procedure given in Example 5.

TABLE 5a

![structure: Ph2CH-C(O)-N(H)-Y-Z]

| Ex # | Compound | Y—Z | Mass Spectrum (MH)+ |
|---|---|---|---|
| | N-(4-Acetyl-phenyl)-2,2-diphenyl-acetamide | [4-acetylphenyl] | 330 |

TABLE 5b

![structure: K/L-CH-C(O)-NH-C6H4-N(Et)2]

| Ex # | Compound | K / L CONH— | Mass Spectrum (MH)+ |
|---|---|---|---|
| | N-(4-Diethylamino-phenyl)-2,3-diphenyl-propionamide | [2,3-diphenylpropionyl] | 373 |
| | 2-Cyclohexyl-N-(4-diethylamino-phenyl)-2-phenyl-acetamide | [2-cyclohexyl-2-phenylacetyl] | 365 |

Example 6

N-(4-Diethylamino-phenyl)-2-phenyl-2-pyrrolidin-1-yl-acetamide

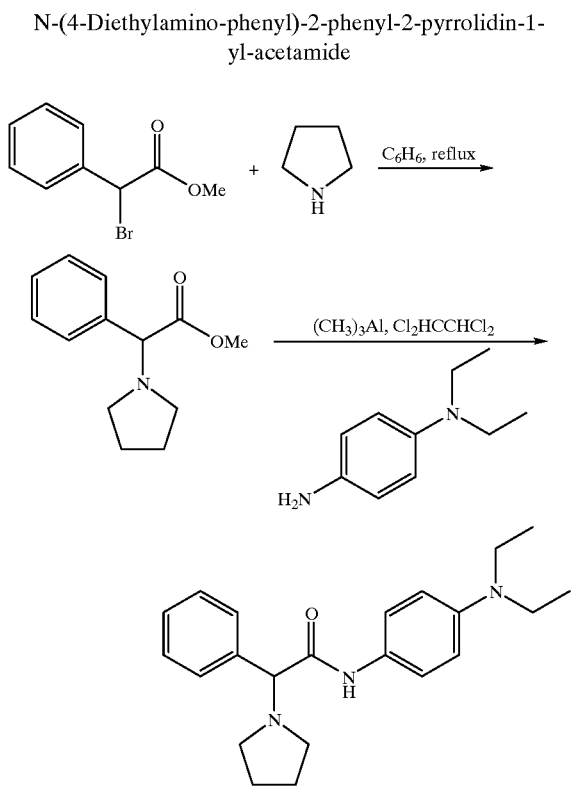

Step A: According to the literature procedure Gloede, J. et al. Arch. Pharm. (Weinheim) 1969, 302, 354–61, piperidine (1.70 mL, 1.4 g, 20.3 mmol, 3.0 equiv) was added in one portion to a solution of methyl 2-bromophenylacetate (1.0 mL, 1.6 g, 6.8 mmol, 1.0 equiv) in benzene (15 mL). The resultant solution was heated to reflux for 16 hours, and then cooled to 23° C. The reaction mixture was extracted twice with 3N hydrochloric acid (25 mL). The combined aqueous extracts were washed once with ether (25 mL) and then the pH was adjusted to 12 with 1N sodium hydroxide. The basic solution was extracted with two portions of ethyl acetate (25 mL), and the combined extracts were dried over magnesium sulfate and concentrated.

Step B: According to the procedure given in Example 6, Step B, the crude methyl 2-phenyl-2-pyrrolidin-1-ylacetate (356 mg, 1.6 mmol, 1.0 equiv) was coupled with N,N-diethylamino-1,3-phenylenediamine (0.81 mL, 0.80 g, 4.8 mmol) using trimethylaluminum (2.4 mL of a 2.0 M solution in hexane, 4.8 mmol) in 1,2-dichloroethane (20 mL). Standard work-up provided a residue that was purified by flash column chromatography (20% THF/hexanes) to afford the title compound (268 mg). MS: 352 (M+1)

The compounds in Table 6 were prepared according to the procedure given in Example 6.

TABLE 6

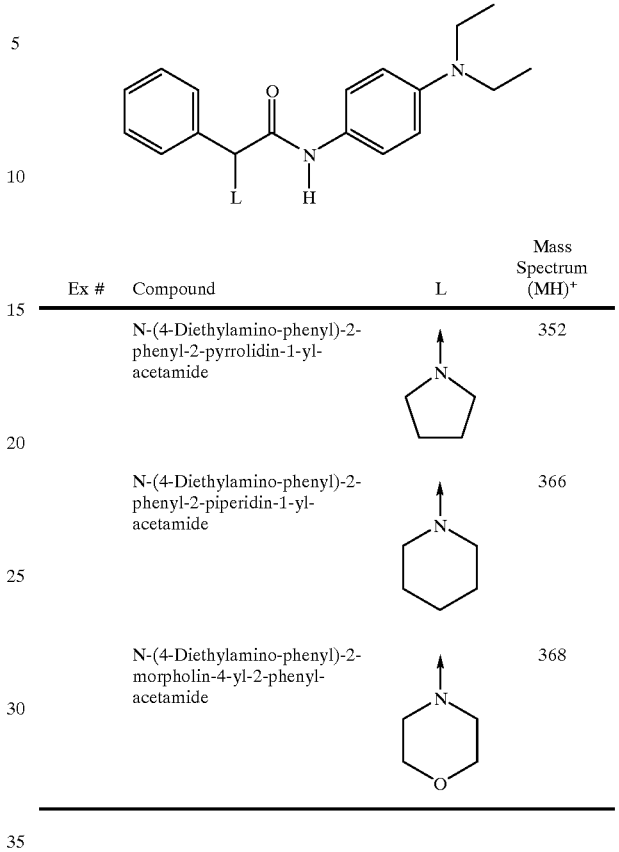

| Ex # | Compound | L | Mass Spectrum (MH)+ |
|---|---|---|---|
| | N-(4-Diethylamino-phenyl)-2-phenyl-2-pyrrolidin-1-yl-acetamide | pyrrolidinyl | 352 |
| | N-(4-Diethylamino-phenyl)-2-phenyl-2-piperidin-1-yl-acetamide | piperidinyl | 366 |
| | N-(4-Diethylamino-phenyl)-2-morpholin-4-yl-2-phenyl-acetamide | morpholinyl | 368 |

Example 7

N-(6-Diethylamino-pyridin-3-yl)-2,2-diphenyl-acetamide

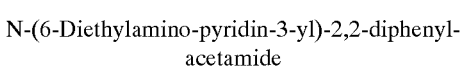

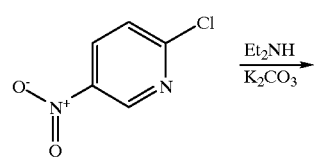

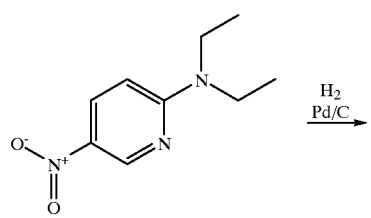

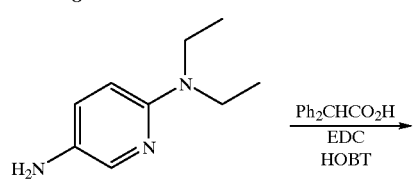

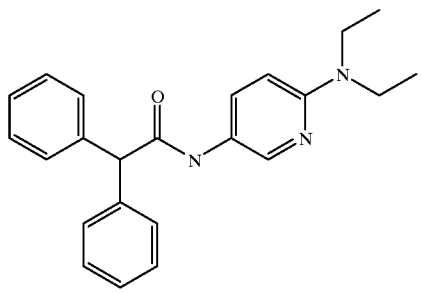

Step A: A mixture of 2-chloro-5-nitropyridine (1100 mg, 6.83 mmol), diethylamine (500 mg, 6.83 mmol) and $K_2CO_3$ (1130 mg, 8.20 mmol) in DMF (30 mL) was stirred at room temperature for 16 h. The reaction mixture was diluted with IPE (300 mL) and was washed with sat'd aq $NaHCO_3$, sat'd aq NaCl, dried and concentrated in vacuo. The crude residue was chromatographed on $SiO_2$-gel (10% EAH) to give the desired product (1300 mg).

Step B: The product from Step 1 was hydrogenated on a Parr Shaker using 250 mg of Pd/C in EtOH (250 mL) at 20 psi. The reaction mixture was filtered thru celite and concentrated in vacuo to give the desired product (1080 mg).

Step C: The crude product from Step 2 (141 mg) was coupled to diphenylacetic acid using HOBT and EDC in DMF using the procedure described in Example 1. The crude residue was dissolved in 10% HCl and the solid that crashed out of solution was filtered to give the title compound (130 mg).

The compounds in Table 7 were prepared according to the procedure given in Example 7.

TABLE 7

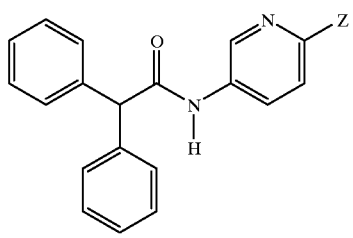

| Ex # Compound | Z | Mass Spectrum |
|---|---|---|
| N-(6-Diethylamino-pyridin-3-yl)-2,2-diphenyl-acetamide | | 360 |
| N-(6-Dimethylamino-pyridin-3-yl)-2,2-diphenyl-acetamide | | 332 |
| 2,2-Diphenyl-N-(6-pyrrolidin-1-yl-pyridin-3-yl)-acetamide | | 358 |

TABLE 7-continued

| Ex # Compound | Z | Mass Spectrum |
|---|---|---|
| 2,2-Diphenyl-N-(3,4,5,6-tetrahydro-2H-[1,2']bipyridinyl-5'-yl)-acetamide | | 373 |
| N-(6-Morpholin-4-yl-pyridin-3-yl)-2,2-diphenyl-acetamide | | 374 |
| N-[6-(2,5-Dimethyl-pyrrolidin-1-yl)-pyridin-3-yl]-2,2-diphenyl-acetamide | | 386 |

Example 8

4-Diphenylacetylamino-N,N-dimethyl-benzamide

Step A: To a solution of the 4-diphenylacetylamino-benzoic acid ethyl ester (6200 mg, 16.7 mmol) in EtOH (50 mL) was added 2N NaOH (2 M solution, 25 mL). The reaction mixture was stirred at 50° C. for 17 h, cooled to room temperature and concentrated in vacuo. The residue was dissolved in water, acidified with citric acid, and extracted with CHCl₃ (2×100 mL). The combined organic extracts were dried and concentrated to give the product as a white solid (4500 mg).

Step B: A solution of 4-diphenylacetylamino-benzoic acid (150 mg, 0.45 mmol), dimethylamine (2.0 M in THF, 203 mg, 0.24 mL, 4.5 mmol), EDC (86 mg, 0.45 mmol) and HOBT (61 mg, 0.45 mmol) in CH₂Cl₂ (15 mL) was stirred at room temperature for 17 h. The reaction mixture was diluted with CHCl₃ and washed with 10 N HCl (4 mL), sat'd aq NaHCO₃ (4 mL) and sat'd aq brine. The organic solution was dried and concentrated in vacuo to give the title compound as a white solid (100 mg).

The compounds in the Table 8 were prepared by the procedure described in Example 8.

TABLE 8

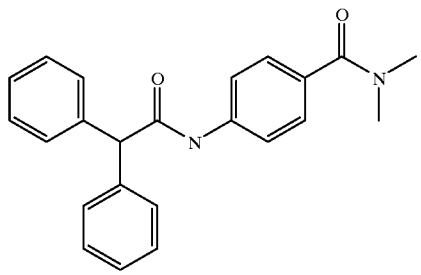

| Ex # | Name | —NR₁R₂ | Mass Spectrum (MH)⁺ |
|---|---|---|---|
| | 4-Diphenylacetylamino-N,N-diethyl-benzamide | | 387 |
| | N-Benzyl-4-diphenylacetylamino-benzamide | | 422 (M + 2H) |
| | 4-Diphenylacetylamino-N-pyridin-2-ylmethyl-benzamide | | 423 (M + 2H) |
| | N-[4-(Morpholine-4-carbonyl)-phenyl]-2,2-diphenyl-acetamide | | 401 |
| | 2,2-Diphenyl-N-[4-(piperazine-1-carbonyl)-phenyl]-acetamide | | 401 |

Example 9

N-(4-Diethylsulfamoyl-phenyl)-2,2-diphenyl-acetamide

Step A: Diethylamine (0.815 mL, 576 mg, 7.86 mmol) was added in one portion to a solution of 4-nitrobenzenesulfonyl chloride (582 mg, 2.62 mmol) in dichloromethane (10 mL). The resultant solution was stirred at 23° C. for 14 hours and then washed twice with 1N HCl (15 mL). The organics were dried over magnesium sulfate and concentrated to provide N,N-Diethyl-4-nitro-benzenesulfonamide as an off-white solid (617 mg).

Step B: A 250 mL Parr shaker bottle was charged with N,N-Diethyl-4-nitro-benzenesulfonamide (617 mg, 2.39 mmol), ethyl acetate (50 mL), and 10% palladium on activated carbon (100 mg). The bottle was place on a Parr shaker apparatus and charged with hydrogen to a pressure of 52 psi. The reaction mixure was shaken for two hours, filtered through celite, and concentrated to provide 4-Amino-N,N-diethyl-benzenesulfonamide as a green solid (581 mg).

Step C: A solution of diphenylacetic acid (223 mg, 1.05 mmol), 4-Amino-N,N-diethyl-benzenesulfonamide (240 mg, 1.05 mmol), HOBT (213 mg, 1.58 mmol), and EDC (242 mg, 1.26 mmol) in dichloromethane (20 mL) was stirred at 23° C. for 15 hours. The reaction mixture was washed with 1N aqueous sodium hydroxide (10 mL), 1N aqueous hydrochloric acid (10 mL), and saturated aqueous sodium chloride (10 mL). The organics were dried over magnesium sulfate and were concentrated. Flash chromatography (20% THF in hexanes grading to 40% THF in hexanes) provided the title compound as orange oil that solidified upon standing (224 mg). MS 423 (M+1)

The compounds in the Table 9 were prepared by the procedure described in Example 9.

TABLE 9

| Ex # | Name | —R | Mass Spectrum (MH)+ |
|---|---|---|---|
| | N-(4-Diethylsulfamoyl-phenyl)-2,2-diphenyl-acetamide | | 423 |
| | N-(4-Dimethylsulfamoyl-phenyl)-2,2-diphenyl-acetamide | | 395 |
| | 2,2-Diphenyl-N-[4-(piperidine-1-sulfonyl)-phenyl]-acetamide | | 435 |
| | 2,2-Diphenyl-N-[4-(pyrrolidine-1-sulfonyl)-phenyl]-acetamide | | 421 |
| | N-[4-(Morpholine-4-sulfonyl)-phenyl]-2,2-diphenyl-acetamide | | 435 (M—H)+ |

TABLE 9-continued

| Ex # | Name | —R | Mass Spectrum (MH)+ |
|---|---|---|---|
| | N-[4-(4-Methyl-piperazine-1-sulfonyl)-phenyl]-2,2-diphenyl-acetamide | | 450 |
| | N-(4-Cyclohexylsulfamoyl-phenyl)-2,2-diphenyl-acetamide | | 447 (M—H)+ |
| | N-(4-Dicyclohexylsulfamoyl-phenyl)-2,2-diphenyl-acetamide | | 531 |
| | N-(4-Benzylsulfamoyl-phenyl)-2,2-diphenyl-acetamide | | 455 (M—H)+ |
| | N-(4-Dibutylsulfamoyl-phenyl)-2,2-diphenyl-acetamide | | 477 (M—H)+ |
| | N-(4-Diisopropylsulfamoyl-phenyl)-2,2-diphenyl-acetamide | | 451 |
| | N-[4-(Azetidine-1-sulfonyl)-phenyl]-2,2-diphenyl-acetamide | | 407 |

What is claimed is:
1. A compound of the formula:

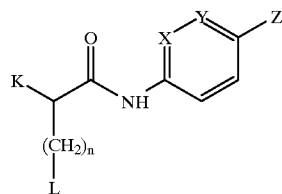

wherein:
K is phenyl, 2-pyridyl, 3-pyridyl or 4-pyridyl, each ring optionally substituted with one to three substituents selected from halogen, $C_1$–$C_3$ alkyl, $C_1$–$C_3$ perfluoroalkyl, $C_1$–$C_3$ alkoxy and $C_1$–$C_3$ perfluoroalkoxy;
L is H, $C_3$–$C_8$ cycloalkyl,

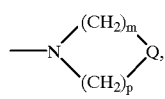

phenyl, 2-pyridyl, 3-pyridyl or 4pyridyl;
wherein each phenyl and pyridyl ring may be substituted with one to three substituents selected from $C_1$–$C_3$ alkyl, $C_1$–$C_3$ alkoxy and halogen;
Z is —$COR^3$, —$CONR^1R^2$, —$NR^1R^2$ and $SO_2R^4$;
X and Y are CH or N, with the proviso that one of X and Y must be CH;
n is an integer from 0 to 3;
m and p are independently selected from the integers 1 to 3;
Q is O, NR, CHR;
R is hydrogen or $C_1$–$C_6$ alkyl;
$R^1$ and $R^2$ are independently selected from hydrogen, $C_1$–$C_6$ alkyl, $(CH_2)_m$ phenyl, $(CH_2)_m$ pyridyl, or $R^1$ and $R^2$ may be taken together with the nitrogen to which they are attached to form a 4 to 8 numbered ring optionally containing O, NH or NR; $R^3$ is $C_1$–$C_6$ alkyl; $R^4$ is —$NR^1R^2$,
$R^3$ is $C_1$–$C_6$ alkyl; $R^4$ is —$NR^1R^2$,

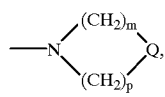

—$NH(CH_2)_m$ phenyl, —$N(C_4$–$C_8$ cycloalkyl$)_2$ and —$NH(C_4$–$C_8$ cycloalkyl); or a pharmaceutically acceptable salt thereof;
and with the provisos that:
when n is zero, K and L are phenyl, and both of X and Y are carbon, then Z is not —$N(C_2H_5)_2$;
when K is phenyl, L is not hydrogen;
when K and L are both phenyl and both X and Y are CH, then Z is not $CONR^1R^2$ or $SO_2NR^1R^2$, wherein $R^1$ and $R^2$ are hydrogen or $C_1$–$C_6$ alkyl; and
when n is O, K is phenyl, L is cyclohexane and both X and Y are CH, then Z is not $SO_2NH_2$.

2. A compound of claim 1 wherein n is zero.
3. A compound of claim 2 wherein L is 2-pyridyl or 4-pyridyl.
4. A compound of claim 3 wherein Z is —$N(C_2H_5)_2$,

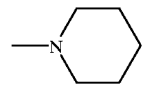

or —$SO_2N(C_2H_5)_2$.
5. A compound of claim 2 wherein Y is N and Z is

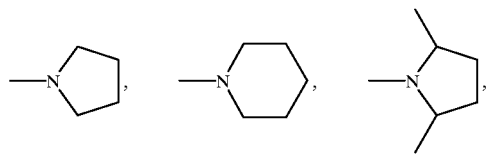

6. A compound of claim 2 wherein Z is —$SO_2R^4$ and $R^4$ is —$N(C_2H_5)_2$ or —$N(CH_3)_2$.
7. A compound of claim 1 which is selected from:
N-(4-Diethylamino-phenyl)-2-phenyl-2-pyridin-4-yl-acetamide;
2-(4-Fluoro-phenyl)-2-pyridin-4-yl-N-(3,4,5,6-tetrahydro-2H-[1,2']bipyridinyl-5'-yl)-acetamide;
2-Phenyl-2-pyridin-4-yl-N-(3,4,5,6-tetrahydro-2H-[1,2']bipyridinyl-5'-yl)-acetamide;
N-(4-Diethylamino-phenyl)-2-phenyl-2-pyridin-2-yl-acetamide;
N-(6-Diethylamino-pyridin-3-yl)-2,2-diphenylacetamide;
N-(4-Diethyl-sulfamoyl-phenyl)-2-phenyl-2-pyridin-4-yl-acetamide;
2,2-Diphenyl-N-(6-pyrrolidin-1-yl-pyridin-3-yl)-acetamide;
2,2-Diphenyl-N-(3,4,5,6-tetrahydro-2H-[1,2']bipyridinyl-5'-yl)-acetamide;
N-[6-(2,5-Dimethyl-pyrrolidin-1-yl)-pyridin-3-yl]-2,2-diphenyl-acetamide;
N-(4-Diethylsulfamoyl-phenyl)-2,2-diphenyl-acetamide; and
N-(4-Dimethylsulfamoyl-phenyl)-2,2-diphenyl-acetamide.
8. A method of treating a pathological condition or physiological disorder in a mammal characterized by or associated with an excess of neuropeptide Y which comprises administering to a mammal in need of such treatment a neuropeptide Y inhibiting amount of a compound of the formula

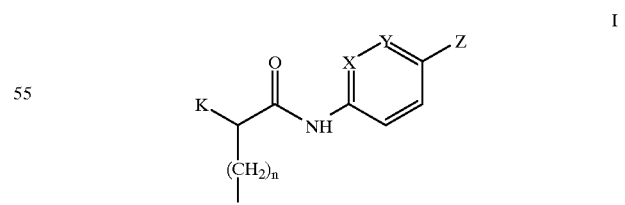

wherein:
K is phenyl, 2-pyridyl, 3-pyridyl or 4-pyridyl, each ring optionally substituted with one to three substituents selected from halogen, $C_1$–$C_3$ alkyl, $C_1$–$C_3$ perfluoroalkyl, $C_1$–$C_3$ alkoxy and $C_1$–$C_3$ perfluoroalkoxy;

L is H, $C_3$–$C_8$ cycloalkyl,

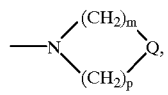

phenyl, 2-pyridyl, 3-pyridyl or 4-pyridyl;
wherein each phenyl and pyridyl ring may be substituted with one to three substituents selected from $C_1$–$C_3$ alkyl, $C_1$–$C_3$ alkoxy and halogen;

Z is —$COR^3$, —$CONR^1R^2$, —$NR^1R^2$ and $SO_2R^4$;

X and Y are CH or N, with the proviso that one of X and Y must be CH;

n is an integer from 0 to 3;

m and p are independently selected from the integers 1 to 3;

Q is O, NR, CHR;

R is hydrogen or $C_1$–$C_6$ alkyl;

$R^1$ and $R^2$ are independently selected from hydrogen, $C_1$–$C_6$ alkyl, $(CH_2)_m$ phenyl, $(CH_2)_m$ pyridyl, or $R^1$ and $R^2$ may be taken together with the nitrogen to which they are attached to form a 4 to 8 numbered ring optionally containing O, NH or NR; $R^3$ is $C_1$–$C_6$ alkyl; $R^4$ is —$NR^1R^2$, $R^3$ is $C_1$–$C_6$ alkyl; $R^4$ is —$NR^1R^2$,

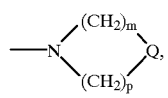

—$NH(CH_2)_m$ phenyl, —$N(C_4$–$C_8$ cycloalkyl$)_2$ and —$NH(C_4$–$C_8$ cycloalkyl); or a pharmaceutically acceptable salt thereof;

and with the proviso that:

when n is zero, K and L are phenyl, and both of X and Y are carbon, then Z is not —$N(C_2H_5)_2$;

when K is phenyl, L is not hydrogen; and when K and L are both phenyl and both X and Y are CH, then Z is not $CONR^1R^2$ or $SO_2NR^1R^2$, wherein $R^1$ and $R^2$ are hydrogen or $C_1$–$C_6$ alkyl.

9. A method of claim 8 wherein said pathological condition or physiological disorder is a feeding disorder.

10. A method of claim 8 wherein said pathological condition or physiological disorder is selected from the group consisting of:

disorders or diseases pertaining to the heart, blood vessels or the renal system;

conditions related to increased sympathetic nerve activity;

cerebral diseases and diseases related to the central nervous system;

conditions related to pain or nociception;

diseases related to abnormal gastrointenstinal motility and secretion;

abnormal drink and food intake disorders;

diseases related to sexual dysfunction and reproductive disorders;

conditions or disorders associated with inflammation;

respiratory diseases; and diseases related to abnormal hormone release.

11. A pharmaceutical composition which comprises the compound of claim 1 or a pharmaceutically acceptable salt thereof and a pharmaceutically acceptable carrier.

12. A method of claim 9 wherein said feeding disorder is selected from obesity and bulimia.

13. A method of claim 10 wherein said disorders or diseases pertaining to the heart, blood vessels or the renal system are selected from vasospasm, heart failure, shock, cardiac hypertrophy, increased blood pressure, angina, myocardial infarction, sudden cardiac death, arrythmia, peripheral vascular disease, impaired flow of fluid of the renal system, abnormal mass transport of the renal system and renal failure.

14. A method of claim 10 wherein said conditions related to increased sympathetic nerve activity are selected from conditions that occur during coronary artery surgery, conditions that occur after coronary artery surgery and conditions related to operations and surgery in the gastrointestinal tract.

15. A method of claim 10 wherein said cerebral diseases and diseases related to the central nervous system are selected from cerebral infarction, neurodegeneration, epilepsy, stroke, conditions related to stroke, cerebral vasospasm and hemorrhage, depression, anxiety, schizophrenia, and dementia.

16. A method of claim 10 wherein said diseases related to abnormal gastrointenstinal motility and secretion are selected from different forms of ileus, urinary incontinence and Crohn's disease.

17. A method of claim 10 wherein said abnormal drink and food intake disorders is selected from anorexia and metabolic disorders.

18. A method of claim 10 wherein said respiratory diseases are selected from asthma, conditions related to asthma and bronchoconstriction.

19. A method of claim 10 wherein said diseases related to abnormal hormone release are selected from, diseases related to abnormal leutinizing hormone release, diseases related to abnormal growth hormone release, diseases related to abnormal insulin release and diseases related to abnormal prolactin release.

* * * * *